(12) United States Patent
Rodeville et al.

(10) Patent No.: US 8,901,357 B2
(45) Date of Patent: Dec. 2, 2014

(54) DIBENZOYL PEROXIDE DERIVATIVES, PREPARATION METHOD THEREOF AND COSMETIC OR DERMATOLOGICAL COMPOSITIONS CONTAINING SAME

(75) Inventors: Nicolas Rodeville, Mandelieu (FR); Jean-Claude Pascal, Nice (FR); Claire Bouix-Peter, Vallauris (FR)

(73) Assignee: Galderma Research & Development, Biot (FR)

( * ) Notice: Subject to any disclaimer, the term of this patent is extended or adjusted under 35 U.S.C. 154(b) by 43 days.

(21) Appl. No.: 13/519,871

(22) PCT Filed: Dec. 22, 2010

(86) PCT No.: PCT/FR2010/052876
§ 371 (c)(1), (2), (4) Date: Nov. 16, 2012

(87) PCT Pub. No.: WO2011/080469
PCT Pub. Date: Jul. 7, 2011

(65) Prior Publication Data
US 2013/0079544 A1    Mar. 28, 2013

(30) Foreign Application Priority Data
Dec. 29, 2009  (FR) ...................................... 09 59630

(51) Int. Cl.
*C07C 409/32* (2006.01)
*A61K 31/075* (2006.01)
*C07C 409/34* (2006.01)

(52) U.S. Cl.
CPC ........... *C07C 409/34* (2013.01); *C07C 2103/74* (2013.01); *C07C 2101/04* (2013.01); *C07C 2101/08* (2013.01); *C07C 2101/02* (2013.01); *C07C 2101/14* (2013.01)
USPC ........................... 568/566; 568/567; 514/714

(58) Field of Classification Search
CPC  C07C 409/34; C07C 409/36; C07C 2101/02; A61K 31/327
USPC .................................... 568/566, 567; 514/714
See application file for complete search history.

(56) References Cited

U.S. PATENT DOCUMENTS
4,364,940 A    12/1982  Neiss et al.

OTHER PUBLICATIONS

International Search Report issued on May 9, 2011 by the European Patent Office as the International Searching Authority in International Patent Application No. PCT/FR2010/052876, and an English language translation of the Search Report.

*Primary Examiner* — Sikarl Witherspoon
(74) *Attorney, Agent, or Firm* — Dentons US LLP

(57) ABSTRACT

The use of compounds in the treatment of skin disorders is described. In particular, compounds having the general formula (I):

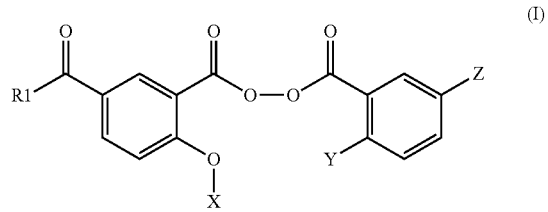

are described.

A process for preparing such compounds and their cosmetic or dermatological use are also described.

The described compounds can act as bactericides. As a result, they can be useful in the treatment of conditions associated with the presence of bacteria, more specifically of *P. acnes*.

8 Claims, 1 Drawing Sheet

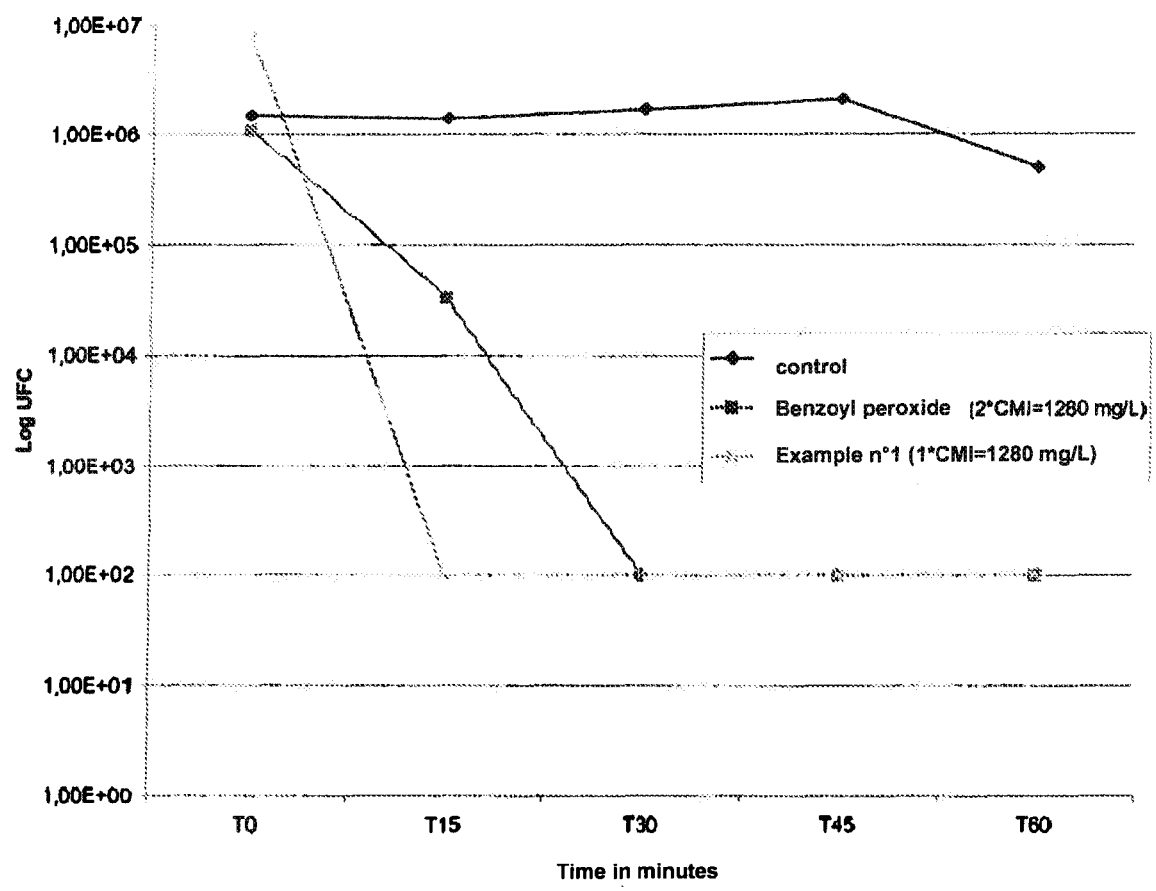

DIBENZOYL PEROXIDE DERIVATIVES, PREPARATION METHOD THEREOF AND COSMETIC OR DERMATOLOGICAL COMPOSITIONS CONTAINING SAME

CROSS-REFERENCE TO PRIOR APPLICATIONS

This application is a National Stage of PCT/FR2010/052876, filed Dec. 22, 2010, and designating the United States (published in French on Jul. 7, 2011, as WO 2011/080469 A1; the title and abstract were published in English), which claims priority of FR 0959630, filed Dec. 29, 2009, each hereby expressly incorporated by reference in its entirety and each assigned to the assignee hereof.

TECHNICAL FIELD

The present invention relates to the use of the compounds of general formula (I) below:

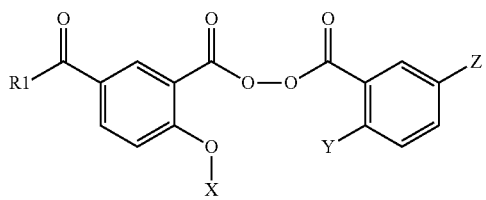

(I)

The invention also relates to a process for preparing them and to their cosmetic or dermatological use.

The compounds of the present invention act as bactericides. As a result, they are useful in the treatment of conditions associated with the presence of bacteria, more specifically of *P. acnes*.

The present invention also relates to the use of compounds corresponding to general formula (I) in cosmetic compositions.

BACKGROUND

It is known that the cutaneous flora is very varied, aerobic or anaerobic, composed especially of *Staphylococcus epidermis* and *aureus* and other micrococci, aerobic corynebacteria, enterobacteria such as *Escherichia coli, Klebsiella* and *Proteus*, or propionibacteria, in relative proportions that depend on the anatomical location, as mentioned, for example, by J. Fleurette in the Revue du Praticien -30(51) pp. 3471-3480 (1980).

Thus, antimicrobial agents that inhibit bacterial proliferation are now commonly introduced into body deodorant compositions.

The use of antimicrobial agents in dermatology and body hygiene is also necessary.

SUMMARY

One subject of the present invention is thus compounds with antimicrobial action, intended for cutaneous application, of general formula (I) below:

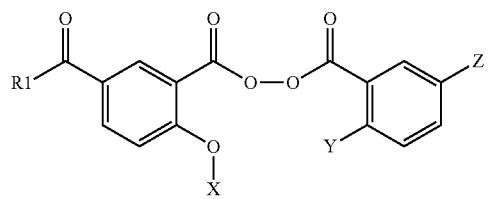

in which:
R1 represents a lower alkyl or a higher alkyl;
X represents a hydrogen or one of the following sequences:

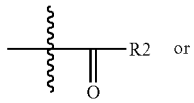

(a)

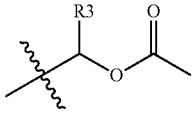

(b)

If X represents (a), R2 represents a lower alkyl, a higher alkyl, a cycloalkyl, a cycloalkylalkyl, a lower alkoxy, a higher alkoxy, a cycloalkyloxy, a cycloalkylalkoxy, an aryl or an aryloxy;
If X represents (b), R3 represents a hydrogen or a lower alkyl;
Y represents a hydrogen or the following sequence:

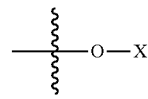

Z represents a hydrogen or the following sequence:

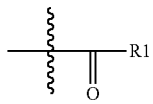

According to the present invention, the preferred compounds corresponding to the general formula (I) are those that have the following characteristics:
R1 represents a linear heptyl chain;
X represents a hydrogen or one of the following sequences:

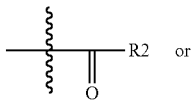

(a)

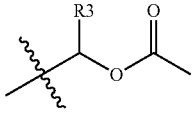

(b)

If X represents (a), R2 represents a lower alkyl, a higher alkyl, a cycloalkyl, a cycloalkylalkyl, a lower alkoxy, a higher alkoxy, a cycloalkyloxy, a cycloalkylalkoxy, an aryl or an aryloxy;

If X represents (b), R3 represents a hydrogen or a methyl group;

Y represents a hydrogen or the following sequence:

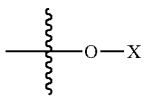

Z represents a hydrogen or the following sequence:

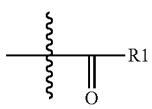

Still according to the present invention, the particularly preferred compounds of general formula (I) are those for which:

R1 represents a linear heptyl chain;
X represents a hydrogen or one of the following sequences:

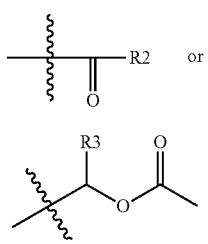

If X represents (a), R2 represents a lower alkyl, a higher alkyl, a cycloalkyl, a lower alkoxy or a higher alkoxy;

If X represents (b), R3 represents a hydrogen or a methyl group;

Y represents a hydrogen or the following sequence:

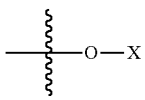

Z represents a hydrogen.

BRIEF DESCRIPTION OF FIGURES

FIG. 1, provides the evaluation of the bactericidal effect on a strain of *P. acnes* UAA 2284.

DETAILED DESCRIPTION

According to the present invention, the term "lower alkyl" denotes a linear or branched, saturated hydrocarbon-based chain comprising from 1 to 4 carbon atoms.

According to the present invention, the term "higher alkyl" denotes a linear or branched, saturated hydrocarbon-based chain comprising from 5 to 10 carbon atoms.

According to the present invention, the term "cycloalkyl" denotes a saturated cyclic, bicyclic or tricyclic hydrocarbon-based chain comprising from 3 to 10 carbon atoms.

According to the present invention, the term "cycloalkylalkyl" denotes an alkyl substituted with a cycloalkyl.

According to the present invention, the term "aryl" means an unsubstituted phenyl or naphthyl.

According to the present invention, the term "lower alkoxy" denotes an oxygen atom substituted with a lower alkyl.

According to the present invention, the term "higher alkoxy" denotes an oxygen atom substituted with a higher alkyl.

According to the present invention, the term "cycloalkoxy" denotes an oxygen atom substituted with a cycloalkyl.

According to the present invention, the term "cycloalkylalkoxy" denotes an oxygen atom substituted with a cycloalkylalkyl.

According to the present invention, the term "aryloxy" denotes an oxygen atom substituted with an aryl.

Among the compounds of general formula (I) which fall within the context of the present invention, mention may be made especially of the following compounds:

Example 1: (2-acetoxy-5-octanoylbenzoyl)benzoyl peroxide

Example 2: (2-ethoxycarbonyloxy-5-octanoylbenzoyl)benzoyl peroxide

Example 3: (2-propionyloxy-5-octanoylbenzoyl)benzoyl peroxide

Example 4: (2-butyryloxy-5-octanoylbenzoyl)benzoyl peroxide

Example 5: (2-isobutyryloxy-5-octanoylbenzoyl)benzoyl peroxide

Example 6: [2-(2,2-dimethylpropionyloxy)-5-octanoylbenzoyl]benzoyl peroxide

Example 7: (2-pentanoyloxy-5-octanoylbenzoyl)benzoyl peroxide

Example 8: [2-(2-methylbutyryloxy)-5-octanoylbenzoyl]benzoyl peroxide

Example 9: [2-(3-methylbutyryloxy)-5-octanoylbenzoyl]benzoyl peroxide

Example 10: (2-hexanoyloxy-5-octanoylbenzoyl)benzoyl peroxide

Example 11: [2-(2-ethylbutyryloxy)-5-octanoylbenzoyl]benzoyl peroxide

Example 12: [2-(3,3-dimethylbutyryloxy)-5-octanoylbenzoyl]benzoyl peroxide

Example 13: (2-heptanoyloxy-5-octanoylbenzoyl)benzoyl peroxide

Example 14: (2-octanoyloxy-5-octanoylbenzoyl)benzoyl peroxide

Example 15: (2-nonanoyloxy-5-octanoylbenzoyl)benzoyl peroxide

Example 16: (2-cyclopropanecarbonyloxy-5-octanoylbenzoyl)benzoyl peroxide

Example 17: (2-cyclobutanecarbonyloxy-5-octanoylbenzoyl)benzoyl peroxide

Example 18: (2-cyclopentanecarbonyloxy-5-octanoylbenzoyl)benzoyl peroxide

Example 19: (2-cyclohexanecarbonyloxy-5-octanoylbenzoyl)benzoyl peroxide

Example 20: (2-benzoyloxy-5-octanoylbenzoyl)benzoyl peroxide

Example 21: [2-(adamantane-1-carbonyloxy)-5-octanoylbenzoyl]benzoyl peroxide

Example 22: [2-(2-adamantan-1-ylacetoxy)-5-octanoylbenzoyl]benzoyl peroxide

Example 23: (2-methoxycarbonyloxy-5-octanoylbenzoyl) benzoyl peroxide
Example 24: (2-propoxycarbonyloxy-5-octanoylbenzoyl) benzoyl peroxide
Example 25: (2-isopropoxycarbonyloxy-5-octanoylbenzoyl)benzoyl peroxide
Example 26: (2-tert-butoxycarbonyloxy-5-octanoylbenzoyl)benzoyl peroxide
Example 27: (2-butoxycarbonyloxy-5-octanoylbenzoyl) benzoyl peroxide
Example 28: (2-sec-butoxycarbonyloxy-5-octanoylbenzoyl)benzoyl peroxide
Example 29: (2-isobutoxycarbonyloxy-5-octanoylbenzoyl)benzoyl peroxide
Example 30: (2-pentoxycarbonyloxy-5-octanoylbenzoyl) benzoyl peroxide
Example 31: [2-(1-ethylpropoxycarbonyloxy)-5-octanoylbenzoyl]benzoyl peroxide
Example 32: [2-(2,2-dimethyl propoxycarbonyloxy)-5-octanoylbenzoyl]benzoyl peroxide
Example 33: (2-hexyloxycarbonyloxy-5-octanoylbenzoyl)benzoyl peroxide
Example 34: (2-heptyloxycarbonyloxy-5-octanoylbenzoyl)benzoyl peroxide
Example 35: (2-octyloxycarbonyloxy-5-octanoylbenzoyl) benzoyl peroxide
Example 36: (2-cyclopropoxycarbonyloxy-5-octanoylbenzoyl)benzoyl peroxide
Example 37: (2-cyclobutoxycarbonyloxy-5-octanoylbenzoyl)benzoyl peroxide
Example 38: (2-cyclopentoxycarbonyloxy-5-octanoylbenzoyl)benzoyl peroxide
Example 39: (2-cyclohexyloxycarbonyloxy-5-octanoylbenzoyl)benzoyl peroxide
Example 40: (2-phenoxycarbonyloxy-5-octanoylbenzoyl) benzoyl peroxide
Example 41: (2-acetoxymethoxy-5-octanoylbenzoyl)benzoyl peroxide
Example 42: [2-(1-acetoxyethoxy)-5-octanoylbenzoyl] benzoyl peroxide
Example 43: bis(2-acetoxy-5-octanoyl)benzoyl peroxide
Example 44: bis(2-propionyloxy-5-octanoyl)benzoyl peroxide
Example 45: bis(2-butyryloxy-5-octanoyl)benzoyl peroxide
Example 46: bis(2-isobutyryloxy-5-octanoyl)benzoyl peroxide
Example 47: bis[2-(2,2-dimethylpropionyloxy)-5-octanoyl]benzoyl peroxide
Example 48: bis(2-pentanoyloxy-5-octanoyl)benzoyl peroxide
Example 49: bis[2-(2-methyl butyryloxy)-5-octanoyl]benzoyl peroxide
Example 50: bis[2-(3-methyl butyryloxy)-5-octanoyl]benzoyl peroxide
Example 51: bis(2-hexanoyloxy-5-octanoyl)benzoyl peroxide
Example 52: bis[2-(2-ethyl butyryloxy)-5-octanoyl]benzoyl peroxide
Example 53: bis[2-(3,3-dimethylbutyryloxy)-5-octanoyl] benzoyl peroxide
Example 54: bis(2-heptanoyloxy-5-octanoyl)benzoyl peroxide
Example 55: bis(2-octanoyloxy-5-octanoyl)benzoyl peroxide
Example 56: bis(2-nonanoyloxy-5-octanoyl)benzoyl peroxide
Example 57: bis(2-cyclopropanecarbonyloxy-5-octanoyl) benzoyl peroxide
Example 58: bis(2-cyclobutanecarbonyloxy-5-octanoyl) benzoyl peroxide
Example 59: bis(2-cyclopentanecarbonyloxy-5-octanoyl) benzoyl peroxide
Example 60: bis(2-cyclohexanecarbonyloxy-5-octanoyl) benzoyl peroxide
Example 61: bis(2-benzoyloxy-5-octanoyl)benzoyl peroxide
Example 62: bis[2-(adamantane-1-carbonyloxy)-5-octanoyl]benzoyl peroxide
Example 63: bis[2-(2-adamantan-1-ylacetoxy)-5-octanoyl]benzoyl peroxide
Example 64: bis(2-methoxycarbonyloxy-5-octanoyl)benzoyl peroxide
Example 65: bis(2-ethoxycarbonyloxy-5-octanoyl)benzoyl peroxide
Example 66: bis(2-propoxycarbonyloxy-5-octanoyl)benzoyl peroxide
Example 67: bis(2-isopropoxycarbonyloxy-5-octanoyl) benzoyl peroxide
Example 68: bis(2-tert-butoxycarbonyloxy-5-octanoyl) benzoyl peroxide
Example 69: bis(2-butoxycarbonyloxy-5-octanoyl)benzoyl peroxide
Example 70: bis(2-sec-butoxycarbonyloxy-5-octanoyl) benzoyl peroxide
Example 71: bis(2-isobutoxycarbonyloxy-5-octanoyl) benzoyl peroxide
Example 72: bis(2-pentoxycarbonyloxy-5-octanoyl)benzoyl peroxide
Example 73: bis[2-(1-ethylpropoxycarbonyloxy)-5-octanoyl]benzoyl peroxide
Example 74: bis[2-(2,2-dimethylpropoxycarbonyloxy)-5-octanoyl]benzoyl peroxide
Example 75: bis(2-hexyloxycarbonyloxy-5-octanoyl)benzoyl peroxide
Example 76: bis(2-heptyloxycarbonyloxy-5-octanoyl) benzoyl peroxide
Example 77: bis(2-octyloxycarbonyloxy-5-octanoyl)benzoyl peroxide
Example 78: bis(2-cyclopropoxycarbonyloxy-5-octanoyl) benzoyl peroxide
Example 79: bis(2-cyclobutoxycarbonyloxy-5-octanoyl) benzoyl peroxide
Example 80: bis(2-cyclopentoxycarbonyloxy-5-octanoyl) benzoyl peroxide
Example 81: bis(2-cyclohexyloxycarbonyloxy-5-octanoyl)benzoyl peroxide
Example 82: bis(2-phenoxycarbonyloxy-5-octanoyl)benzoyl peroxide
Example 83: bis(2-acetoxymethoxy-5-octanoyl)benzoyl peroxide
Example 84: bis[2-(1-acetoxyethoxy)-5-octanoyl]benzoyl peroxide A general description of methods for preparing the compounds of formula (I) is given below. In these schemes and in the description of the process that follows, unless otherwise specified, all the substituents are as defined for the compounds of formula (I).

In the case where the group Y defined in formula (I) is a hydrogen and the group Z defined in formula (I) is a hydrogen, the compounds of general formula (I) are prepared according to reaction scheme 1 or reaction scheme 2 presented below.

Scheme 1

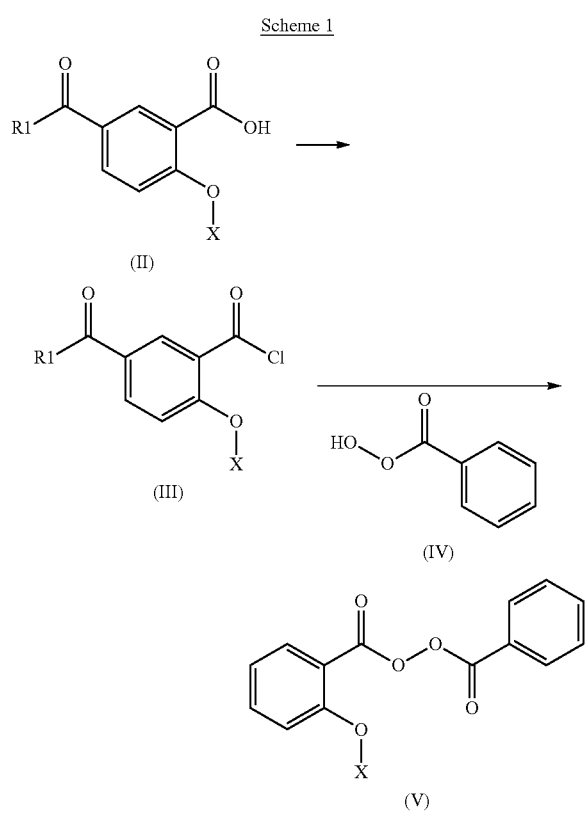

According to scheme 1, the acid chlorides of general formula (III) are prepared from the carboxylic acid (II), via methods chosen among those known to a person skilled in the art. They include the use of thionyl chloride and pyridine in a solvent such as toluene or dichloromethane, for example.

The carboxylic acids of general formula (II) are commercially available or are prepared according to the methods described in scheme 5.

In a final step, the compounds of general formula (V) may be prepared by coupling between the acyl chlorides of formula (III) and the peracid of formula (IV), using pyridine as base in a mixture of solvents such as dichloromethane and chloroform.

The peracid of general formula (IV) is prepared according to the method described in scheme 6 from benzoyl peroxide.

Scheme 2

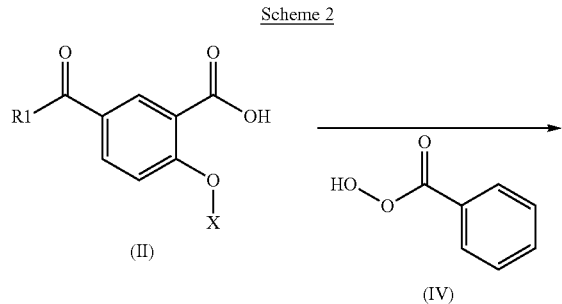

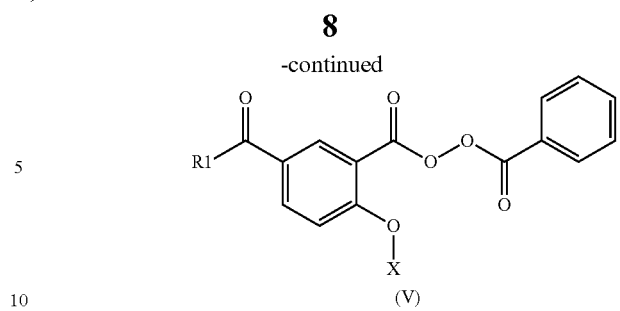

According to scheme 2, the peroxides of general formula (V) are prepared by coupling between the carboxylic acids of formula (II) and the peracid of formula (IV), using, for example, as coupling agent N,N'-dicyclohexylcarbodiimide, for example in a mixture of solvents such as diethyl ether and dichloromethane.

The carboxylic acids of general formula (II) are commercially available or are prepared according to the methods described in scheme 5.

The peracid of general formula (IV) is prepared according to the method described in scheme 6 from benzoyl peroxide.

In the case where the groups Y and Z defined in formula (I) are not a hydrogen, the compounds of general formula (I) are prepared according to reaction scheme 3 or reaction scheme 4 presented below.

Scheme 3

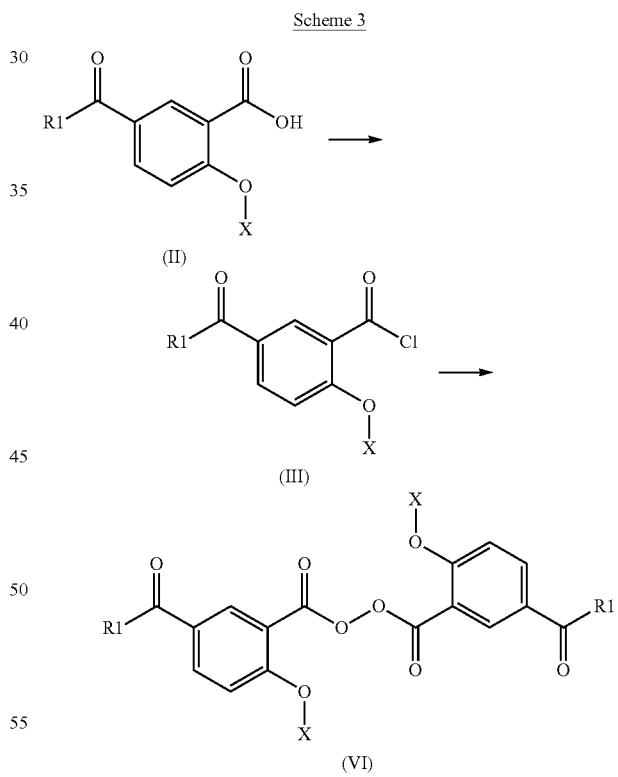

According to scheme 3, the acid chlorides of general formula (III) are prepared from the carboxylic acid (II), via methods chosen among those known to a person skilled in the art. They include the use of thionyl chloride and pyridine in a solvent such as toluene or dichloromethane, for example.

The carboxylic acids of general formula (II) are prepared according to the methods described in scheme 5.

In a final step, the compounds of general formula (VI) may be prepared by coupling between two acyl chlorides of formula (III) via methods chosen from those known to a person skilled in the art. They include the use of hydrogen peroxide and sodium bicarbonate in a solvent such as tetrahydrofuran, for example.

Scheme 4

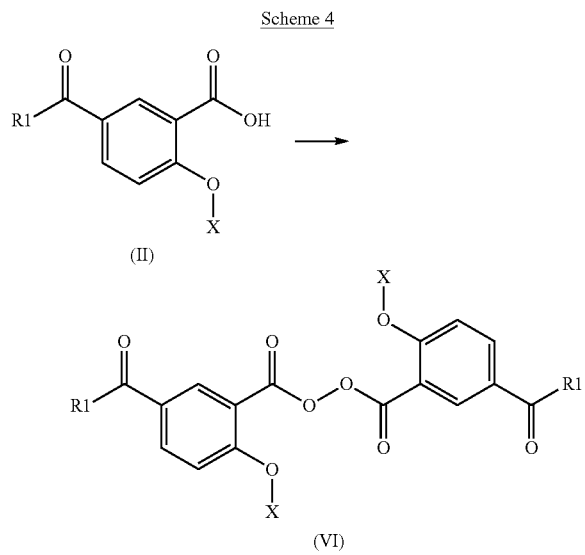

(II)

(VI)

According to scheme 4, the peroxides of general formula (VI) are prepared by reaction between two carboxylic acids of formula (II), using, for example, N,N'-dicyclohexylcarbodiimide and hydrogen peroxide in a mixture of solvents such as diethyl ether and dichloromethane.

In the case where X is not a hydrogen, the carboxylic acids of formula (II) may be prepared according to reaction scheme 5.

Scheme 5

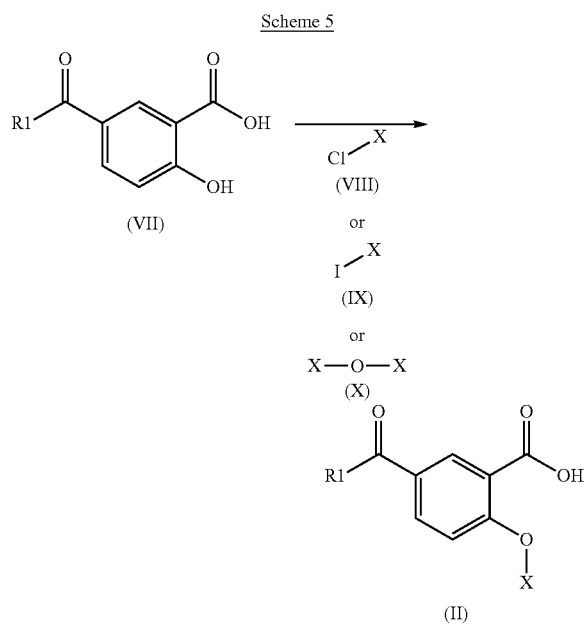

(VII)

(VIII)

or (IX)

or

X—O—X
(X)

(II)

According to scheme 5, the carboxylic acids of formula (II) are prepared from the carboxylic acid (VII) via methods chosen from those known to a person skilled in the art. They include the use of halides of formulae (VIII) and (IX) or anhydrides of formula (X), and of bases such as N,N-dimethylaniline, triethylamine, pyridine or potassium carbonate, in a solvent such as toluene or dichloromethane, for example. The halides of formulae (VIII) and (IX) and the anhydrides of formula (X) are commercially available.

In the case where X is a hydrogen, the carboxylic acids of formula (II) are commercially available.

The peracid of formula (IV) may be prepared according to reaction scheme 6.

Scheme 6

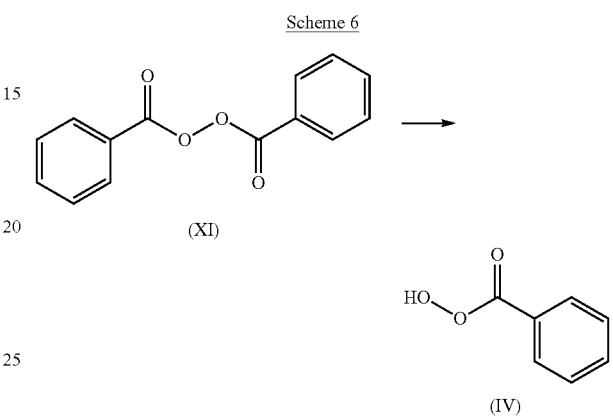

(XI)

(IV)

According to scheme 6, the peracid of formula (IV) is prepared from dibenzoyl peroxide (XI), via methods chosen among those known to a person skilled in the art. They include the use of a peroxide (XI) and sodium in a mixture of solvents such as methanol and chloroform, for example.

Study of the Sensitivity of Peroxides Versus Dibenzoyl Peroxide on *Propionibacterium acnes*

Assay Principle:

The aim is to evaluate the antibacterial activity of peroxides by measuring the Minimum Inhibitory Concentrations (MIC). The MIC is defined as being the lowest concentration of product that is capable of inhibiting any growth visible to the naked eye. The MICs are determined via an international reference method: "Methods For Antimicrobial Susceptibility Testing of Anaerobic Bacteria; Approved Standard, Seventh Edition" M11A7 of the CLSI (Clinical Laboratory Standards institute), dilution method in agar medium.

Microbial Strain and Origin:

The product sensitivity study is performed on ten strains of *P. acnes* isolated from human pathological samples. In order to check the validity and reproducibility of the results obtained, three reference strains recommended by standard M 11 A7 are introduced into each series of tests: *Bacteroides fragilis* ATCC 25285, *Bacteroides thetaiotaomicron* ATCC 29741, *Eubacterium lentum* ATCC 43055, *Clostridium difficile* ATCC 700057.

Product Assay:

The products are dissolved at 1280 mg/L in a mixture of absolute ethanol/Tween 80/sterile *Brucella* culture medium (5/10/85 v/v/v). Twofold serial dilutions are performed in sterile distilled water starting with this stock solution and according to the directives of Ericsson and Sherris. The range is composed of 8 concentrations from 10 mg/L to 1280 mg/L, at doubling intervals.

A preculture in Rosenow medium is diluted in *Brucella* broth so as to obtain opacity in the region of 0.5 on the McFarland scale. The inoculum then contains $10^7$ to $10^8$ cfu/ml.

Using a Steers multi-headed seeder, 2 to 3 µl of inoculum, deposited beforehand in each of the cups of the seeder, are deposited in the Petri dishes. The final inoculum is about $10^5$ cfu per inoculation spot.

The results are read after 48 hours of incubation in an anaerobic chamber. The MIC is defined as being the lowest concentration of product that is capable of inhibiting any visible growth.

| Test strain | Benzoyl peroxide MIC in mg/L | Example 1 MIC in mg/L |
| --- | --- | --- |
| CSS 2971 | 640 | 320 |
| CSS 2913 | 640 | 320 |
| CSS 3288 | 640 | 320 |
| 1044 | 640 | 320 |
| 1045 | 640 | 320 |
| 1201 | 640 | 320 |
| 3069 | 640 | 1280 |
| 998 | 640 | 1280 |
| UAA 2281 | 640 | 320 |
| UAA 2285 | 640 | 320 |

Evaluation of the Bactericidal Effect of the Molecules Versus Dibenzoyl Peroxide on *Propionibacterium acnes*

Assay Principle:

The aim is to evaluate the bactericidal effect from the Minimum Inhibitory Concentration (MIC) measurement performed beforehand. The methodology proposed for evaluating the bactericidal activity is inspired from standard NF EN 1040 "Quantitative suspension test for the evaluation of basic bactericidal activity of chemical disinfectants and antiseptics" and T72-300 "Dilution-neutralization suspension test—Determination of the efficacy of products on various microorganisms under practical conditions of use".

Since antiseptics act after a contact time, it is necessary to block their action with a neutralizer.

Microbial Strain and Origin:

The evaluation of the bactericidal effect is performed on a strain of *P. acnes* UAA 2284 (isolated from human pathological samples).

Product Assay:

First, a control tube of *Brucella* culture medium and a tube containing the neutralizing solution are prepared. The products are dissolved in a mixture of absolute ethanol/Tween 80 (7/3 v/v). The following dilutions are performed in sterile distilled water. The concentration used in each test is, depending on the test, from one to four times the MIC.

The *P. acnes* strain is inoculated in the *Brucella* broth and then incubated at 35-36° C. for 48 hours. A dilution of this preculture is then performed in *Brucella* broth so as to obtain cloudiness equivalent to that of the 0.5 calibration tube on the McFarland scale, i.e. an inoculum of about $10^7$-$10^8$ cfu/ml. 1 ml of the control tube (control or neutralizer) or 1 ml of the 10× solution of test product (assay) is placed in contact with 9 ml of the inoculum prepared previously: i.e. a final inoculum in the test tube of about $10^7$ cfu/ml.

After 0, 15 minutes, 30 minutes, 45 minutes and 1 hour of contact with the test product, 100 µl of the test tube are taken up and placed immediately in 900 µl of neutralizing solution. Counting of the survivors is then performed and the bactericidal activity is defined as being a reduction of three logarithms $\log_{10}$ of the starting inoculum (FIG. 1 below).

Example 1

(2-acetoxy-5-octanoylbenzoyl)benzoyl peroxide 1-1: 2-acetoxy-5-octanoylbenzoic acid 6 g (22.7 mmol) of 2-hydroxy-5-octanoylbenzoic acid and 12 mL (0.145 mol) of pyridine are dissolved in 15 mL of acetone. The medium is cooled to 0° C., and 12 mL (0.166 mol) of acetyl chloride are then added dropwise. After stirring for 15 hours at room temperature, water is added and the mixture is extracted with dichloromethane. The organic phase is dried over magnesium sulfate, filtered and then concentrated. 7 g of 2-acetyloxy-5-octanoylbenzoic acid are obtained in the form of a white solid in quantitative yield.

1-2: 2-Acetoxy-5-octanoylbenzoyl chloride 5.5 g (18 mmol) of 2-acetyloxy-5-octanoylbenzoic acid are dissolved in 55 ml of dichloromethane with one drop of pyridine. 1.6 ml (21.5 mmol) of thionyl chloride are added dropwise and the mixture is stirred at 35° C. for 18 hours and then concentrated to dryness. 5.6 g of 2-acetoxy-5-octanoylbenzoyl chloride are obtained in the form of a red oil in a yield of 96%.

1-3: Perbenzoic acid 19 g (78 mmol) of dibenzyl peroxide are dissolved in 125 ml of chloroform at −5° C. 2.2 g (94 mmol) of sodium dissolved in 50 ml of methanol under a stream of nitrogen are added dropwise. After stirring for 30 minutes at −5° C., ice-cold water is added and the medium is acidified with aqueous 2N sulfuric acid solution. Extraction with dichloromethane is performed and the organic phase is then dried over magnesium sulfate, filtered and concentrated. 9 g of perbenzoic acid are obtained in the form of a white solid in a yield of 83%.

1-4: (2-acetoxy-5-octanoylbenzoyl)benzoyl peroxide 5.5 g (16.9 mmol) of 2-acetoxy-5-octanoylbenzoyl chloride and 3.5 g (25.4 mmol) of perbenzoic acid are dissolved in 22 ml of chloroform. The mixture is cooled to −18° C., and 1.14 g (14.4 mmol) of pyridine in 3 ml of dichloromethane are then added dropwise. After stirring for 1 hour at −18° C., water is added and the mixture is extracted with dichloromethane. The organic phase is dried over sodium sulfate, filtered and then concentrated. The residue is purified by chromatography on silica gel eluted with a 1/1 pentane/dichloromethane mixture. The yellow solid obtained is precipitated from pentane at −18° C. The precipitate is filtered off and then rinsed with pentane and dried. 2 g of (2-acetoxy-5-octanoyl)benzoyl peroxide are obtained in the form of a white powder in a yield of 28%.

$^1$H NMR 300 MHz/CDCl$_3$: δ=0.91 (m, 3H); 1.37 (m, 8H); 1.77 (m, 2H); 2.41 (s, 3H); 3.02 (t, J=10 Hz, 2H); 7.35 (d, J=12 Hz, 1H); 7.55 (dd, J=12 Hz, 2H); 7.72 (m, 1H); 8.09 (d, J=12 Hz, 2H); 8.27 (d, J=12 Hz, 1H); 8.63 (s, 1H)

Example 2

(2-ethoxycarbonyloxy-5-octanoylbenzoyl)benzoyl peroxide 2-1: 2-Ethoxycarbonyloxy-5-octanoylbenzoic acid 4.89 g (18.50 mmol) of 2-hydroxy-5-octanoylbenzoic acid and 9 ml (70.30 mmol) of N,N-dimethylaniline are dissolved in 30 ml of toluene. The medium is cooled to 0° C., and 1.77 ml (18.50 mmol) of ethyl chloroformate are then added dropwise. After stirring for 2 hours at room temperature, the mixture is washed with aqueous 0.5N hydrochloric acid solution and then with water. The organic phase is dried over magnesium sulfate, filtered and concentrated. 5.59 g of 2-ethoxycarbonyloxy-5-octanoylbenzoic acid are obtained in the form of a white solid in a yield of 89%.

2-2: 2-Ethoxycarbonyloxy-5-octanoylbenzoyl chloride 5.59 g (16.6 mmol) of 2-ethoxycarbonyloxy-5-octanoylbenzoic acid are dissolved in 56 ml of toluene with a few drops of pyridine. 1.45 ml (20 mmol) of thionyl chloride are added dropwise and the mixture is stirred at 55° C. for 14 hours and then concentrated to dryness. 5.79 g of 2-ethoxycarbonyloxy-5-octanoylbenzoyl chloride are obtained in a yield of 98%.

2-3: (2-ethoxycarbonyloxy-5-octanoylbenzoyl)benzoyl peroxide

In a manner similar to that of Example 1-4, starting with 5.79 g (16.3 mmol) of 2-ethoxycarbonyloxy-5-octanoylbenzoyl chloride and 3.38 g (24.5 mmol) of perbenzoic acid (prepared as described in Example 1-3), 2 g of (2-ethoxycarbonyloxy-5-octanoyl)benzoyl peroxide are obtained in the form of a colourless oil in a yield of 26%.

$^1$H NMR 300 MHz/CDCl$_3$: δ=0.88 (m, 3H); 1.20 (m, 11H); 1.78 (m, 2H); 3.00 (t, J=6 Hz, 2H); 4.43 (q, J=7 Hz, 2H); 7.42 (d, J=12 Hz, 1H); 7.55 (t, J=12 Hz, 2H); 7.72 (m, 1H); 8.10 (d, J=12 Hz, 2H); 8.27 (d, J=12 Hz, 1H); 8.60 (s, 1H).

The invention claimed is:

1. A compound of the following formula (I):

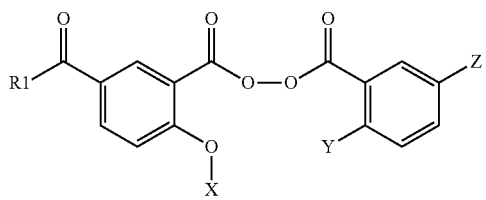

in which:
R1 represents a lower alkyl or a higher alkyl; and
X represents a hydrogen or one of the following sequences:

(a)

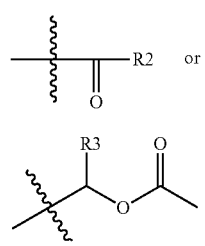

(b)

wherein when X represents (a), R2 represents a lower alkyl, a higher alkyl, a cycloalkyl, a cycloalkylalkyl, a lower alkoxy, a higher alkoxy, a cycloalkyloxy, a cycloalkylalkoxy, an aryl or an aryloxy;

and wherein when X represents (b), R3 represents a hydrogen or a lower alkyl;

Y represents a hydrogen or the following sequence:

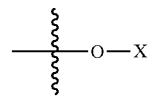

Z represents a hydrogen or the following sequence:

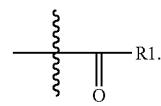

2. A compound as defined by claim 1, wherein:
R1 represents a linear heptyl chain; and
X represents a hydrogen or one of the following sequences:

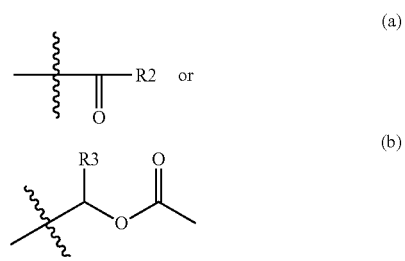

wherein when X represents (a), R2 represents a lower alkyl, a higher alkyl, a cycloalkyl, a cycloalkylalkyl, a lower alkoxy, a higher alkoxy, a cycloalkyloxy, a cycloalkylalkoxy, an aryl or an aryloxy;

and wherein when X represents (b), R3 represents a hydrogen or a methyl group;

Y represents a hydrogen or the following sequence:

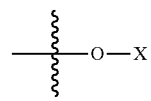

Z represents a hydrogen or the following sequence:

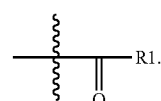

3. A compound as defined by claim 1, wherein:
R1 represents a linear heptyl chain; and
X represents a hydrogen or one of the following sequences:

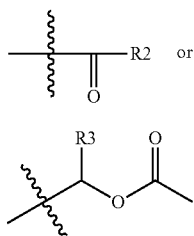 (a)

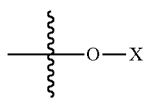 (b)

wherein when X represents (a), R2 represents a lower alkyl, a higher alkyl, a cycloalkyl, a lower alkoxy or a higher alkoxy;
and wherein when X represents (b), R3 represents a hydrogen or a methyl group;
Y represents a hydrogen or the following sequence:

Z represents a hydrogen.

4. The compound according to claim 1, wherein the compound is selected from the group consisting of:
(2-acetoxy-5-octanoylbenzoyl)benzoyl peroxide;
(2-ethoxycarbonyloxy-5-octanoylbenzoyl)benzoyl peroxide;
(2-propionyloxy-5-octanoylbenzoyl)benzoyl peroxide;
(2-butyryloxy-5-octanoylbenzoyl)benzoyl peroxide;
(2-isobutyryloxy-5-octanoylbenzoyl)benzoyl peroxide;
[2-(2,2-dimethylpropionyloxy)-5-octanoylbenzoyl]benzoyl peroxide;
(2-pentanoyloxy-5-octanoylbenzoyl)benzoyl peroxide;
[2-(2-methylbutyryloxy)-5-octanoylbenzoyl]benzoyl peroxide;
[2-(3-methylbutyryloxy)-5-octanoylbenzoyl]benzoyl peroxide;
(2-hexanoyloxy-5-octanoylbenzoyl)benzoyl peroxide;
[2-(2-ethylbutyryloxy)-5-octanoylbenzoyl]benzoyl peroxide;
[2-(3,3-dimethylbutyryloxy)-5-octanoylbenzoyl]benzoyl peroxide;
(2-heptanoyloxy-5-octanoylbenzoyl)benzoyl peroxide;
(2-octanoyloxy-5-octanoylbenzoyl)benzoyl peroxide;
(2-nonanoyloxy-5-octanoylbenzoyl)benzoyl peroxide;
(2-cyclopropanecarbonyloxy-5-octanoylbenzoyl)benzoyl peroxide;
(2-cyclobutanecarbonyloxy-5-octanoylbenzoyl)benzoyl peroxide;
(2-cyclopentanecarbonyloxy-5-octanoylbenzoyl)benzoyl peroxide;
(2-cyclohexanecarbonyloxy-5-octanoylbenzoyl)benzoyl peroxide;
(2-benzoyloxy-5-octanoylbenzoyl)benzoyl peroxide;
[2-(adamantane-1-carbonyloxy)-5-octanoylbenzoyl]benzoyl peroxide;
[2-(2-adamantan-1-ylacetoxy)-5-octanoylbenzoyl]benzoyl peroxide;
(2-methoxycarbonyloxy-5-octanoylbenzoyl)benzoyl peroxide;
(2-propoxycarbonyloxy-5-octanoylbenzoyl)benzoyl peroxide;
(2-isopropoxycarbonyloxy-5-octanoylbenzoyl)benzoyl peroxide;
(2-tert-butoxycarbonyloxy-5-octanoylbenzoyl)benzoyl peroxide;
(2-butoxycarbonyloxy-5-octanoylbenzoyl)benzoyl peroxide;
(2-sec-butoxycarbonyloxy-5-octanoylbenzoyl)benzoyl peroxide;
(2-isobutoxycarbonyloxy-5-octanoylbenzoyl)benzoyl peroxide;
(2-pentoxycarbonyloxy-5-octanoylbenzoyl)benzoyl peroxide;
[2-(1-ethylpropoxycarbonyloxy)-5-octanoylbenzoyl]benzoyl peroxide;
[2-(2,2-dimethylpropoxycarbonyloxy)-5-octanoylbenzoyl]benzoyl peroxide;
(2-hexyloxycarbonyloxy-5-octanoylbenzoyl)benzoyl peroxide;
(2-heptyloxycarbonyloxy-5-octanoylbenzoyl)benzoyl peroxide;
(2-octyloxycarbonyloxy-5-octanoylbenzoyl)benzoyl peroxide;
(2-cyclopropoxycarbonyloxy-5-octanoylbenzoyl)benzoyl peroxide;
(2-cyclobutoxycarbonyloxy-5-octanoylbenzoyl)benzoyl peroxide;
(2-cyclopentoxycarbonyloxy-5-octanoylbenzoyl)benzoyl peroxide;
(2-cyclohexyloxycarbonyloxy-5-octanoylbenzoyl)benzoyl peroxide;
(2-phenoxycarbonyloxy-5-octanoylbenzoyl)benzoyl peroxide;
(2-acetoxymethoxy-5-octanoylbenzoyl)benzoyl peroxide;
[2-(1-acetoxyethoxy)-5-octanoylbenzoyl]benzoyl peroxide;
bis(2-acetoxy-5-octanoyl)benzoyl peroxide;
bis(2-propionyloxy-5-octanoyl)benzoyl peroxide;
bis(2-butyryloxy-5-octanoyl)benzoyl peroxide;
bis(2-isobutyryloxy-5-octanoyl)benzoyl peroxide;
bis[2-(2,2-dimethylpropionyloxy)-5-octanoyl]benzoyl peroxide;
bis(2-pentanoyloxy-5-octanoyl)benzoyl peroxide;
bis[2-(2-methylbutyryloxy)-5-octanoyl]benzoyl peroxide;
bis[2-(3-methylbutyryloxy)-5-octanoyl]benzoyl peroxide;
bis(2-hexanoyloxy-5-octanoyl)benzoyl peroxide;
bis[2-(2-ethylbutyryloxy)-5-octanoyl]benzoyl peroxide;
bis[2-(3,3-dimethylbutyryloxy)-5-octanoyl]benzoyl peroxide;
bis(2-heptanoyloxy-5-octanoyl)benzoyl peroxide;
bis(2-octanoyloxy-5-octanoyl)benzoyl peroxide;
bis(2-nonanoyloxy-5-octanoyl)benzoyl peroxide;
bis(2-cyclopropanecarbonyloxy-5-octanoyl)benzoyl peroxide;
bis(2-cyclobutanecarbonyloxy-5-octanoyl)benzoyl peroxide;
bis(2-cyclopentanecarbonyloxy-5-octanoyl)benzoyl peroxide;
bis(2-cyclohexanecarbonyloxy-5-octanoyl)benzoyl peroxide;
bis(2-benzoyloxy-5-octanoyl)benzoyl peroxide;
bis[2-(adamantane-1-carbonyloxy)-5-octanoyl]benzoyl peroxide,
bis[2-(2-adamantan-1-ylacetoxy)-5-octanoyl]benzoyl peroxide;
bis(2-methoxycarbonyloxy-5-octanoyl)benzoyl peroxide;
bis(2-ethoxycarbonyloxy-5-octanoyl)benzoyl peroxide;
bis(2-propoxycarbonyloxy-5-octanoyl)benzoyl peroxide, bis(2-isopropoxycarbonyloxy-5-octanoyl)benzoyl peroxide;
bis(2-tert-butoxycarbonyloxy-5-octanoyl)benzoyl peroxide;
bis(2-butoxycarbonyloxy-5-octanoyl)benzoyl peroxide;
bis(2-sec-butoxycarbonyloxy-5-octanoyl)benzoyl peroxide;
bis(2-isobutoxycarbonyloxy-5-octanoyl)benzoyl peroxide;
bis(2-pentoxycarbonyloxy-5-octanoyl)benzoyl peroxide;
bis[2-(1-ethylpropoxycarbonyloxy)-5-octanoyl]benzoyl peroxide;
bis[2-(2,2-dimethylpropoxycarbonyloxy)-5-octanoyl] benzoyl peroxide;
bis(2-hexyloxycarbonyloxy-5-octanoyl)benzoyl peroxide;
bis(2-heptyloxycarbonyloxy-5-octanoyl)benzoyl peroxide;
bis(2-octyloxycarbonyloxy-5-octanoyl)benzoyl peroxide;
bis(2-cyclopropoxycarbonyloxy-5-octanoyl)benzoyl peroxide;
bis(2-cyclobutoxycarbonyloxy-5-octanoyl)benzoyl peroxide;
bis(2-cyclopentoxycarbonyloxy-5-octanoyl)benzoyl peroxide;
bis(2-cyclohexyloxycarbonyloxy-5-octanoyl)benzoyl peroxide;
bis(2-phenoxycarbonyloxy-5-octanoyl)benzoyl peroxide;
bis(2-acetoxymethoxy-5-octanoyl)benzoyl peroxide; and
bis[2-(1-acetoxyethoxy)-5-octanoyl]benzoyl peroxide.

5. The compound as defined by claim 1, wherein the compound is a medicinal product.

6. The compound as defined by claim 1, formulated for the treatment of pathologies or disorders linked to the presence of *Propionibacterium acnes*.

7. A cosmetic composition comprising an effective amount of the compound as defined by claim 1, wherein said effective amount inhibits proliferation of pathogenic microorganisms involved in the appearance of an acne-type skin disorder.

8. The cosmetic composition as defined by claim 7, wherein the acne-type skin disorder is *P. acnes*.

* * * * *